(12) United States Patent
Slinger

(10) Patent No.: US 6,361,517 B1
(45) Date of Patent: Mar. 26, 2002

(54) FOOT LIFT ASSIST

(76) Inventor: Douglas A. Slinger, N8425 Sunny Point Rd., Beaver Dam, WI (US) 53916

( * ) Notice: Subject to any disclaimer, the term of this patent is extended or adjusted under 35 U.S.C. 154(b) by 0 days.

(21) Appl. No.: 09/467,580

(22) Filed: Dec. 20, 1999

Related U.S. Application Data

(63) Continuation-in-part of application No. 09/172,895, filed on Oct. 15, 1998, now abandoned.
(60) Provisional application No. 60/062,735, filed on Oct. 23, 1997.

(51) Int. Cl.$^7$ .................................................. A61F 5/00
(52) U.S. Cl. .......................... 602/28; 36/140; 482/79; 482/124
(58) Field of Search ............................. 482/51, 74, 79, 482/80, 124, 125; 602/23, 27–33; 36/71.5, 136, 140; 434/255

(56) References Cited

U.S. PATENT DOCUMENTS

| | | | |
|---|---|---|---|
| 420,178 A | * 1/1890 | Yagn | 482/51 |
| 420,179 A | * 1/1890 | Yagn | 482/51 |
| 440,884 A | * 11/1890 | Yagn | 482/51 |
| 1,608,032 A | * 11/1926 | McNabb | 602/30 |
| 2,097,376 A | * 10/1937 | Marshman | 482/124 |
| 3,295,517 A | * 1/1967 | Stevens | 602/19 |
| 4,329,982 A | 5/1982 | Heaney | |
| 4,566,447 A | 1/1986 | Deis | |
| 5,112,296 A | 5/1992 | Beard et al. | |
| 5,186,701 A | * 2/1993 | Wikinson | 482/125 |
| 5,308,305 A | 5/1994 | Romney | |
| 5,362,295 A | 11/1994 | Nurge | |
| 5,372,565 A | * 12/1994 | Burdenko | 482/124 |
| 5,407,411 A | * 4/1995 | Trainor | 482/95 |
| 5,429,571 A | * 7/1995 | Smith et al. | 482/115 |
| 5,624,360 A | * 4/1997 | Wilkins | 482/129 |
| 5,752,900 A | * 5/1998 | Holland, Jr. | 482/124 |
| 5,865,203 A | * 2/1999 | Villiano | 135/65 |

FOREIGN PATENT DOCUMENTS

| | | | | |
|---|---|---|---|---|
| CH | 150956 | * | 2/1932 | 482/124 |

* cited by examiner

*Primary Examiner*—Mickey Yu
*Assistant Examiner*—Victor Hwang
(74) *Attorney, Agent, or Firm*—Donald Cayen

(57) ABSTRACT

A foot lift assist enables a person with foot drop to walk in a nearly normal manner. The foot lift assist comprises an elastic cord anchored at a person's hip by a belt. A foot strap is worn on the foot generally over the toes of the foot. The elastic cord is connected to a ring on the foot strap that is located to the outside of the longitudinal centerline of the foot. The elastic cord then lies completely to the outside of the leg and knee. When the person removes his weight from the foot, the elastic cord exerts an upward force that bends the leg at the knee and hip and that also pivots the foot upwardly about the ankle. The person can then take a step without his toes dragging on the ground. The foot strap may be fully flexible. Alternately, for walking on abrasive surfaces, the foot strap may have a metal plate bonded under a strap. A heel band attached to the plate and looped around the heel helps retain the foot strap on the foot.

14 Claims, 3 Drawing Sheets

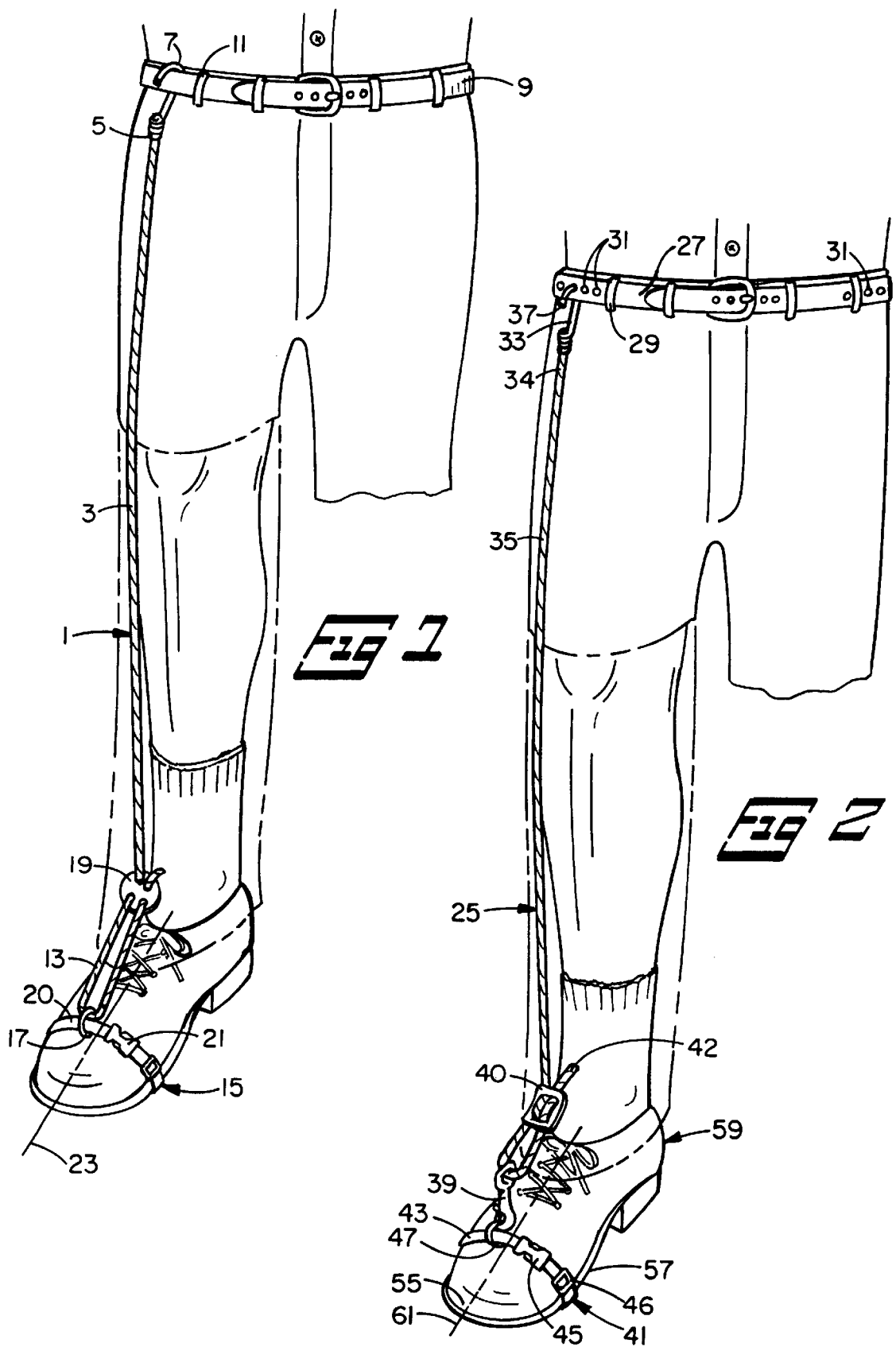

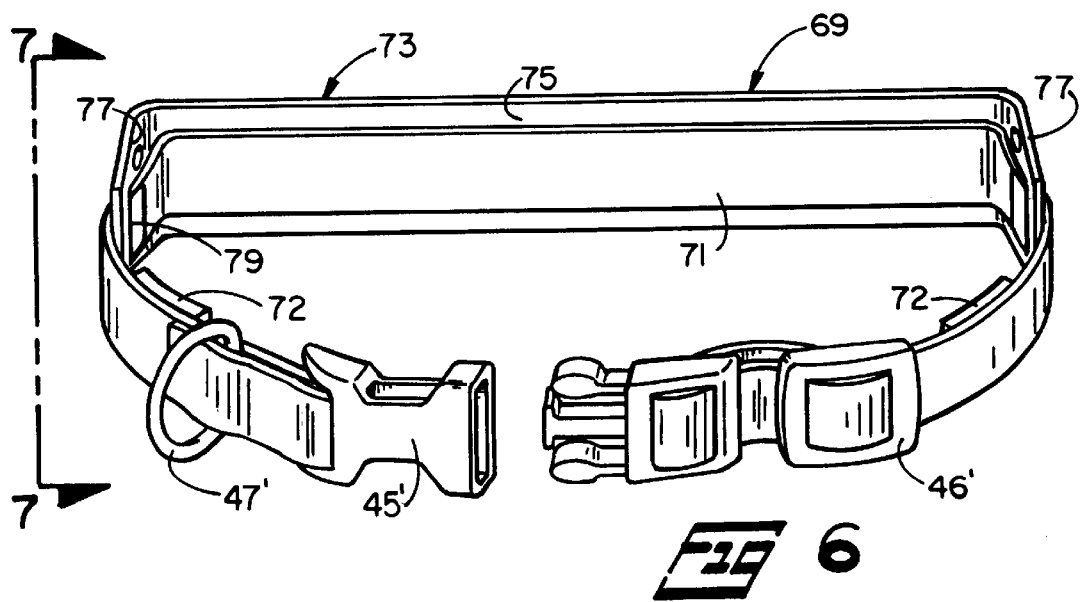
FIG 6
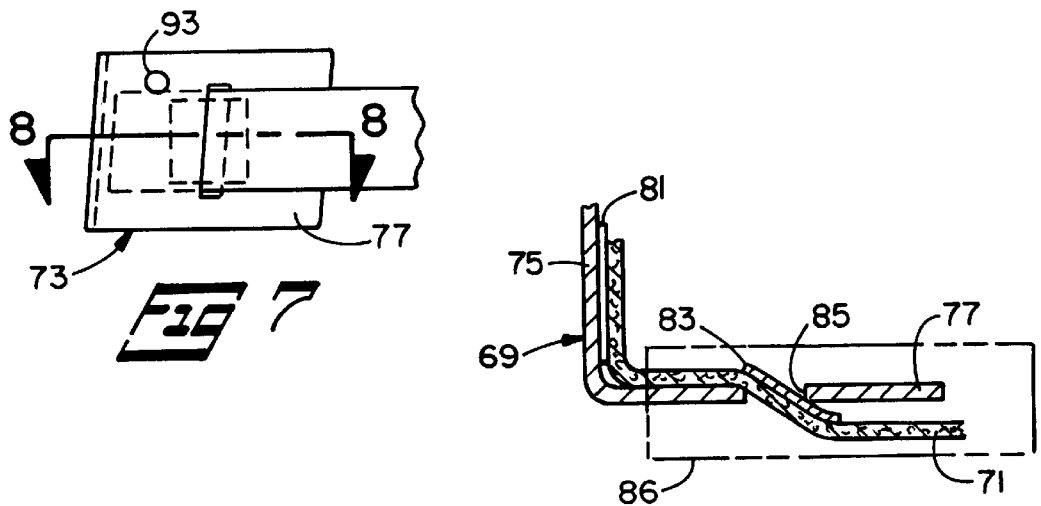
FIG 7
FIG 8
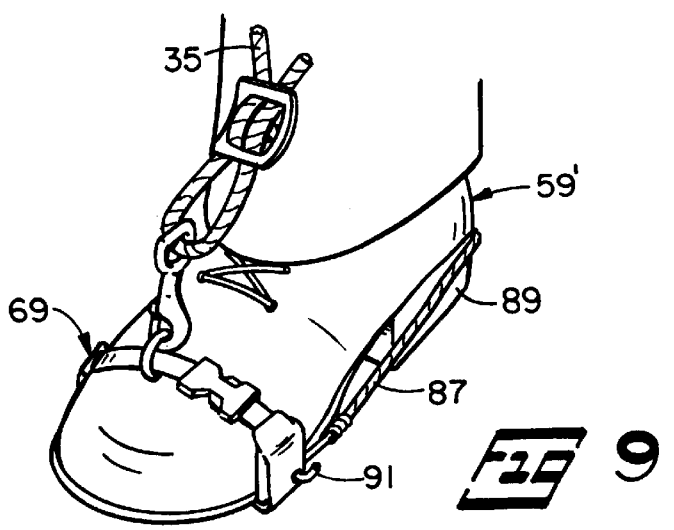
FIG 9

FOOT LIFT ASSIST

This application is a continuation-in-part of U.S. patent application Ser. No. 09/172,895 filed Oct. 15, 1998, now abandoned, which claims the benefit of U.S. Provisional Application Serial No. 60/062,735 filed Oct. 23, 1997.

BACKGROUND OF THE INVENTION

This invention pertains to orthotics, and more particularly to apparatus that assists a person to walk.

DESCRIPTION OF THE PRIOR ART

In normal walking, at the end of each step a rearward foot is in contact with the ground at a distance behind a forward foot. To take another step, the rearward foot must be lifted and swung forwardly through combined actions of the hip, knee, and leg. Simultaneously, the rearward foot must pivot upwardly about the ankle such that the toes lift off the ground.

Some persons, such as those with multiple sclerosis, suffer from a condition commonly known as foot drop. A person with foot drop lacks sufficient muscular control to pivot his foot upwardly about the ankle. In that situation, at the end of a walking step in which the affected foot is behind the forward foot, the person may be able to lift and swing his leg to bring the affected foot forward. However, he is not able to simultaneously pivot his foot upwardly about the ankle. Consequently, if the person makes a normal forward stepping movement with his leg, the toes of the affected foot drag along the ground. A greatly exaggerated lifting of the leg is required to avoid dragging the toes, to the extent that anything remotely resembling normal walking is impossible. In severe cases, the person may have difficulty even bending his knee or swinging his leg from the hip. As a result, such persons are often confined to a wheelchair, or they walk by shuffling their feet using an awkward combination of leg, hip, and knee motions.

Various equipment has been developed to aid persons with foot drop. Examples of such prior devices may be seen in U.S. Pat. Nos. 4,329,982 and 4,566,447. The devices of the two foregoing patents have the disadvantage of requiring modifications to the shoe of the user. In addition, neither aforementioned device is able to assist a person to bend his knee or lift his leg from the hip. A further disadvantage of the device of the U.S. Pat. No. 4,566,447 patent is that the angle of the connection between a leg band and the foot is such that it is difficult to wear with conventional slacks or trousers.

U.S. Pat. Nos. 4,817,589 and 5,257,969 show foot supports that utilize the ankle as an anchor for a strap that goes to the front of the foot or shoe. The constant force on the ankle makes the assists of the U.S. Pat. Nos. 4,817,589 and 5,257,969 patents uncomfortable to wear for long. In addition, the assists of the two foregoing patents do not help a person bend his knee or lift his leg.

U.S. Pat. No. 5,112,296 shows an electronic based orthosis that is quite complicated and expensive. The location of a foot strap between the heel and the ball of the foot provides only minimal leverage for pivoting the foot about the ankle.

Thus, a need exists for an improved way to assist persons suffering from foot drop.

SUMMARY OF THE INVENTION

In accordance with the present invention, a foot lift assist is provided that both enables and encourages a person with foot drop to walk in a nearly normal manner. This is accomplished by an apparatus that includes a long elastic cord extending from a person's hip and acting on his foot forwardly of the ball of the foot.

The foot lift assist is anchored at the person's hip by a belt around his waist. The elastic cord is hooked at one end to the belt over the hip associated with the foot with foot drop. The elastic cord second end is connected by a snap or shackle to a foot strap. The connection point of the elastic cord to the foot strap is to the outside of the longitudinal centerline of the foot.

According to one aspect of the invention, the foot strap is a fully flexible foot strap. The fully flexible foot strap comprises a flexible strap that is adjustable to suit a person's foot or shoe. The flexible strap wraps around the shoe or foot at a location forward of the ball of the foot. To enhance the comfort and performance of the foot lift assist, there is a pad on the inside of the flexible strap that overlies the little toe. The pad is designed to contact the top of the sole of a shoe. In that manner, the flexible strap does not slip circumferentially around the shoe. To further distribute stress in the region of the little toe, a semi-rigid strip can be added between the flexible strap and the pad. Preferably, the outside of the flexible strap under the foot is coated with a non-slip and abrasion resistant material.

When the foot lift assist is in place on a person's affected foot, shifting at least some of his weight to the other foot enables the elastic cord to bend the leg and lift the foot from the ground. The location of the lifting force near the person's toes naturally compensates for foot drop by pivoting the foot upwardly about the ankle. With a little practice, the person is able to walk in a manner that approaches a normal gait. The location of the connection between the elastic cord and the fully flexible foot strap on the outside of the person's foot keeps the elastic cord off the person's knee while he is walking and thus contributes to the performance and comfort of the foot lift assist. The pad provides protection to the little toe during the repeated lifting forces exerted on the flexible strap. The coating on the underside of the flexible strap reduces the possibility of slipping, and it also reduces wear on the flexible strap. The long length of the elastic cord between the belt and the flexible strap enables conventional pants or slacks to be worn without hindering performance of the foot lift assist and without calling attention to the presence of the elastic cord. The snap enables the flexible strap to be quickly disconnected from the elastic cord when the person sits between walking activities.

In a modified embodiment of the invention, the foot strap includes a metal plate that underlies the foot or shoe. The metal plate is useful when a person walks on abrasive surfaces. The metal plate is bonded to a strap. Like the fully flexible foot strap, the connection between the elastic cord and the foot strap with the metal plate is to the outside of the longitudinal centerline of the person's foot.

To assure retention of the metal plate embodiment of the foot strap on the foot, a heel band can be attached to the metal plate at the inside and outside of the foot. The heel band loops around the heel of the foot or shoe. The snap connection between the foot strap and the elastic cord provides easy interchangeability between the fully flexible and metal plate embodiments of the foot strap of the invention.

The method and apparatus of the invention, using a long elastic cord between a person's hip and his foot, thus provides a lifting force to the front of the foot that also lifts the leg. The probability of dragging the toes while walking is remote, even though the person has minimal if any ability to pivot his foot upwardly at the ankle.

Other advantages, benefits, and features of the present invention will become apparent to those skilled in the art upon reading the detailed description of the invention.

BRIEF DESCRIPTION OF THE DRAWINGS

FIG. 1 is a perspective view of the foot lift assist of the invention as worn by a person.

FIG. 2 is a view similar to FIG. 1, but showing a modified embodiment of the invention.

FIG. 6 is a perspective view of a foot strap useful for walking on abrasive surfaces.

FIG. 7 is a view taken along line 7—7 of FIG. 6.

FIG. 8 is a cross-sectional view taken along line 8—8 of FIG. 7.

FIG. 9 is a perspective view showing a heel band on the foot strap.

DETAILED DESCRIPTION OF THE INVENTION

Figure 3:
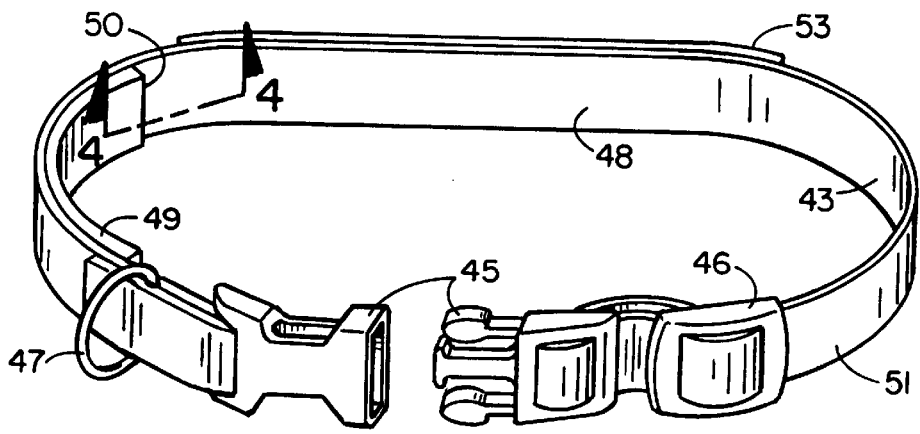
FIG. 3 is a perspective view of the fully flexible foot strap according to the invention.

Although the disclosure hereof is detailed and exact to enable those skilled in the art to practice the invention, the physical embodiments herein disclosed merely exemplify the invention, which may be embodied in other specific structure. The scope of the invention is defined in the claims appended hereto.

Referring first to FIG. 1, a foot lift assist 1 is illustrated that includes the present invention. The foot lift assist 1 is particularly useful for aiding persons with foot drop to walk in a nearly normal manner. However, it will be understood that the invention is not limited to use by persons with multiple sclerosis or other similar disabilities.

The foot lift assist 1 is comprised of a long elastic cord 3 that extends between a person's hip and his affected foot. One end 5 of the elastic cord 3 terminates in a hook 7. The elastic cord end 5 may be anchored to the hip of a person by means of the hook 7 being hooked over the waist band of a pair of trousers. However, I prefer that the hook 7 be hooked over a conventional belt 9 worn through the belt loops 11 of a pair of trousers.

The second end 13 of the elastic cord 3 is connected to a foot strap 15. For that purpose, the foot strap 15 includes a ring 17. The elastic cord passes through the ring 17 and doubles back. An adjustment button 19 provides adjustment to the amount of tension in the elastic cord.

The foot strap 15 includes a length of strong flexible strap material 20. The flexible strap 20 has clips 21 that enable the strap to be opened and closed. The length of the flexible strap is adjustable. The flexible strap is wrappable around the person's foot or shoes forward of the ball of the foot. The ring 17 is toward the outside of the longitudinal centerline 23 of the foot. The long length of the elastic cord relative to the location of the ring 17 results in the elastic cord lying closely alongside the leg. Consequently, the foot lift assist can be worn under a pair of trousers without being noticed.

With proper tension on the elastic cord 3, the elastic cord exerts an upward force on the foot. The person is then able to use the foot lift assist 1 in one of two ways. If the person has some control over his leg and foot, he lifts the foot at least slightly. Doing so inherently takes at least some of the weight off that foot and leg. The foot lift assist is then enabled to continue the more difficult part of taking a step by bending the leg at the hip and knee while simultaneously conserving the person's energy. The location of the foot strap 15 assures that the upward force on the foot raises the front of the foot. The result is that after a minimum of practice, a person can walk in an almost normal fashion. The attachment of the elastic cord to the foot strap on the outside of the foot centerline 23 keeps the elastic cord off the person's knee and thereby adds to the comfort of the foot lift assist. The ability to provide exercise while conserving energy is an important feature of the invention.

If the person is totally paralyzed but is still able to stand, he leans his body toward the side opposite the affected foot. Doing so allows the foot lift assist to bend the leg at the knee and hip and to keep the toes off the ground. The person can then twist his body to swing the leg and foot forwardly in a nearly normal manner.

Figures 4, 4A:
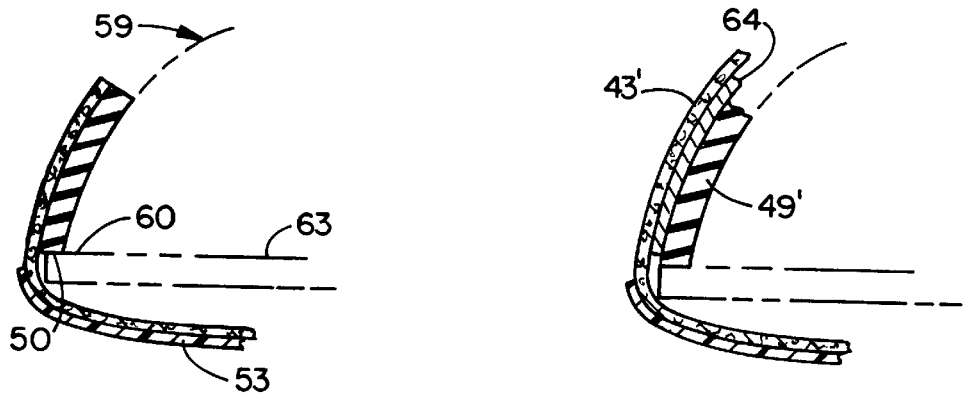
FIG. 4 is a cross-sectional view on an enlarged scale taken along line 4—4 of FIG. 3, but showing the foot strap in place on a person's shoe.
FIG. 4A is a view similar to FIG. 4, but showing a stress strip incorporated into the foot lift assist.

Turning to FIGS. 2–4, a modified foot lift assist 25 comprises a belt 27 with a number of holes 31 through it over the left and right hips. A hook 33 is secured to one end 34 of a long elastic cord 35. A free end of the hook is covered with a protective cap 37. On the second end of the elastic cord 35 is a swivelable snap 39. The elastic cord running end 42 doubles back and is held to the main section of the elastic cord by a Conway buckle 40.

The foot lift assist 25 further comprises a fully flexible foot strap 41. In the illustrated construction, the fully flexible foot strap 41 is made from a flexible strap 43 having two ends. The flexible strap ends are selectively openable and closeable by clips 45. The length of the flexible strap 43 is adjustable by an adjustment buckle 46. A D-ring 47 is held to the flexible strap 43 adjacent to a clip 45. On the inside surface 48 of the flexible strap adjacent the D-ring 47 is a pad 49 of a soft material, such as closed cell neoprene rubber. The pad 49 is preferably slightly wider than the flexible strap and may be approximately 1.50 inches long. The pad has an end 50 opposite the adjacent clip. The outside surface 51 of the flexible strap opposite the clips is coated with a thin layer of a tough abrasion resistant material 53, such as an epoxy adhesive. A satisfactory material is Devcon 5 Minute epoxy marketed by Devcon Consumer Products of Danvers, Mass.

To use the foot lift assist 25, the flexible strap 43 is closed by means of the clips 45. The buckle 46 is adjusted such that the flexible strap fits generally over the toes 55, forwardly of the widest portion 57 of the person's shoe 59. The pad end 50 is placed against the upper surface 60 of the sole 63 of the shoe 59 on the outside of the shoe. In that location, the pad 49 overlies the person's little toe. The D-ring 47 is then to the outside of the longitudinal centerline 61 of the person's foot and shoe.

The belt 27 is worn through the conventional belt loops 29 of a pair of trousers. The hook 33 on the elastic cord 35 is passed through a desired hole 31 in the belt. The elastic cord is placed inside the leg of the person's trousers. The snap 39 is connected to the D-ring 47 to thereby connect the elastic cord to the flexible strap 43. The elastic cord then lies along the outside of the person's leg for the full length of the elastic cord between the belt and the flexible strap.

The desired amount of tension is produced in the elastic cord 35 by means of the Conway buckle 40. The tension is chosen such that removing at least some of the weight from the foot enables the elastic cord to lift the person's leg and foot. The anchor point of the foot lift assist 25 on the person's hip enables the leg to bend at the hip and knee and to swing forwardly and backwardly in a natural manner. Of particular importance is the lifting of the toes 55 relative to the ankle. With the foot lift assist, the toes are lifted off the ground such that the person is able to take steps in a nearly normal manner. In fact, with a little practice, the person is able to climb stairs using the foot lift assist 25. The location of the flexible strap 43 well forward on the person's shoe 59 enhances natural foot pivoting about the ankle while walking and climbing stairs. The pad 49 relieves pressure on the little toe during the repeated cycles of foot lifting and lowering while walking. The end 50 of the pad 49, which is in contact with the shoe sole 63, prevents the flexible strap from slipping around the shoe and thereby assures that the D-ring does not move further away from the foot centerline 61. The abrasion resistant material 53 helps prevent slipping of the flexible strap on the floor, and also resists wear to the flexible strap. The snap 39 is a highly desirable feature of the invention, because it enables a quick and easy connect and disconnect between the elastic cord 35 and the flexible strap. Such connect and disconnect are important when putting the foot lift assist on and taking it off, and also for comfort when sitting between periods of walking.

As mentioned, extended use of the foot lift assist 25 produces repeated applications of lifting force in the region of the person's little toe. To reduce the soreness that sometimes results even with the padding 49, the lifting force is distributed over a wide area. As best shown in FIG. 4A, a semirigid stress strip 64 is interposed between the flexible strap 43' and a pad 49'. The stress strip 64 is joined to both the flexible strap 43' and the pad 49'. The stress strip is preferably approximately two inches long so as to overlie the entire region of the little toe. The width of the stress strip may be the same as that of the flexible strap 43'. Stainless steel approximately 0.03 inches thick is a preferred material for a the stress strip.

Figure 5:
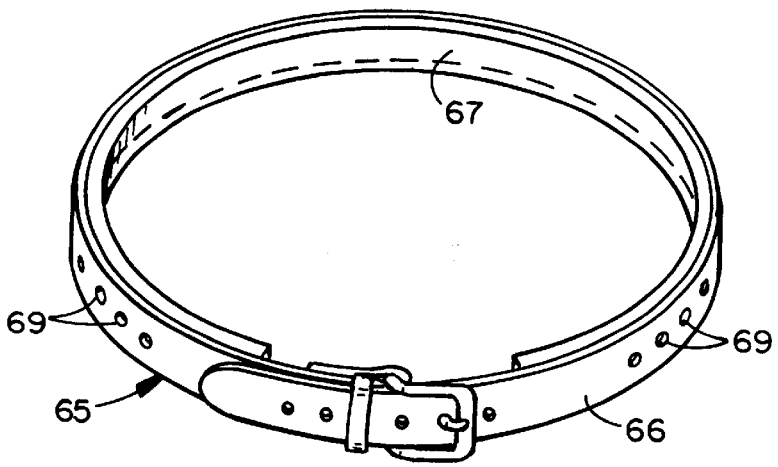
FIG. 5 is a perspective view of a belt used with the invention.

FIG. 5 shows a modified belt 65 according to the present invention. The belt 65 has a generally conventional leather or cloth band 66. A strip of padding 67 is adhered to the inside surface of the band 66. There are holes 69 through both the band and the padding 67 in the hip regions on both sides of the belt. The padded belt 65 is especially useful for wearing against the skin under a person's clothes. In that manner, the person is not limited to wearing a belt outside his clothes. It will be appreciated, of course, that the padded belt 65 can be worn over the person's clothes, if desired, including clothes that do not have belt loops.

Turning to FIGS. 6–8, a modified foot strap 69 is illustrated. The foot strap 69 has a strap 71 that is openable and closeable by clips 45'. The length of the strap 71 is adjustable by a buckle 46'. A D-ring 47' is held to the strap 71. Comfortable pads 72 are bonded to the inside of the strap 71 near the clips 45' and the buckle 46'.

The foot strap 69 further comprises a rigid metal plate 73. A preferred material for the plate 73 is stainless steel approximately 0.06 inches thick. In the illustrated construction, the plate 73 has a base 75 and two upstanding sides 77. Each side 77 has a slot 79 through it. The strap 71 passes through the slots 79. The strap is bonded to the plate along the base 75 with a suitable adhesive 81.

To prevent chafing of the strap 71 on the plate 73 at the slots 79, a protective insert 83 is used in each plate side 77. Each insert 83 is secured to the strap such that the insert lies between the strap and the slot edge 85 further from the plate base 75. In that manner, the repeated force exerted on the strap by the slot edges 85 during use does not damage the strap.

To enhance the appearance of the foot strap 69, a heat shrinkable cover 86 surrounds the plate sides 77 and the flexible strap 71 alongside the plate sides. Consequently, in addition to being unobtrusive, the appearance of the foot strap 69 is aesthetically pleasing. The foot strap 69 is used primarily when walking out of doors on concrete, asphalt, or other abrasive surfaces. The foot strap 69 thus provides longer life than the fully flexible foot strap 41 described previously in conjunction with FIGS. 2–4. The snap 39 enables quick and easy interchangeability between the fully flexible foot strap 41 and the outdoor foot strap 69.

Further in accordance with the present invention, the foot strap 69 is retainable on a person's shoe even when the foot strap is disconnected from the elastic cord 35. Looking also at FIG. 9, a heel band 87 is looped around the heel 89 of the shoe 59'. The heel band 87 may be a short elastic cord with a hook 91 on each end. The hooks 91 are attached to the foot strap 69 by means of a small hole 93 in each side 77 of the plate 73. When the heel band 87 is in place, the foot strap 69 will not fall off the shoe 59' when the foot strap is not connected to the elastic cord 35.

In summary, the walking impairments often associated with multiple sclerosis and similar diseases are greatly alleviated. The foot lift assist provides both increased physical mobility as well as psychological confidence to a person who has trouble walking because of foot drop. This desirable result comes from using the combined functions of the foot strap and the belt. The belt serves as an anchor for the elastic cord at the person's hip, which enables the elastic cord to bend the leg both at the knees and hip. The location of the foot strap well forward of the ankle enables the elastic cord to pivot the foot upwardly about the ankle during walking, further contributing to the effectiveness of the foot lift assist. The fully flexible foot strap 41 is ideal for wearing indoors on non-abrasive surfaces. On the other hand, the foot strap 69 with the metal plate 73 for outdoor use can be quickly interchanged by means of the snap 39 with the fully flexible foot strap. The location of the holes in the belt and on the D-ring on the foot strap keeps the elastic cord off the knee of the person during use, and thereby adds to the comfort of the foot lift assist.

It will also be recognized that in addition to the superior performance of the foot lift assist, its construction as such as to cost no more than traditional walking aids. Also, because it is made of a simple design and with rugged components, it will give long service life with minimal maintenance.

Thus, it is apparent that there has been provided, in accordance with the invention, a foot lift assist that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. In combination:

a) a shoe to be worn by a person and having a sole with a walking surface and an upper surface, the shoe defining a toe end and a heel end and a longitudinal centerline between the toe and heel ends such that there is an inside portion of the shoe on a first side of the longitudinal centerline and an outside portion of the shoe on a second side of the longitudinal centerline, the shoe having a widest section in directions perpendicular to the longitudinal centerline that is closer to the toe end than to the heel end; and b) a foot lift assist comprising:
  i) a belt having opposed lateral sections to be worn over hips of a person;
  ii) a flexible foot strap having inside and outside surfaces and to be worn around the shoe between the toe end and the widest section of the shoe, the flexible foot strap having a first portion that underlies the shoe sole walking surface;
  iii) a ring held on the foot strap at a location on the outside portion of the shoe; and
  iv) an elastic cord having a first end connected to a selected lateral section of the belt, and a second end connected to the ring held on the foot strap,
  v) a pad on the foot strap inside surface and having first and second ends, the pad first end being in flat facing contact with the shoe sole upper surface,
    so that removing the weight of a person wearing the shoe and foot lift assist enables the elastic cord to lift the shoe and pivot the shoe upwardly to thereby enable the person to walk without the shoe toe end dragging on the ground.

2. In combination:
a) a shoe to be worn by a person and having a sole with a walking surface and an upper surface, the shoe defining a toe end and a heel end and a longitudinal centerline between the toe and heel ends such that there is an inside portion of the shoe on a first side of the longitudinal centerline and an outside portion of the shoe on a second side of the longitudinal centerline, the shoe having a widest section in directions perpendicular to the longitudinal centerline that is closer to the toe end than to the heel end: and b) a foot lift assist comprising:
  i) a belt having opposed lateral sections to be worn over hips of a person;
  ii) a flexible foot strap having inside and outside surfaces and to be worn around the shoe between the toe end and the widest section of the shoe, the flexible foot strap having a first portion that underlies the shoe sole walking surface and being in flat facing contact with the shoe sole walking surface;
  iii) a ring held on the foot strap at a location on the outside portion of the shoe;
  iv) an elastic cord having a first end connected to a selected lateral section of the belt, and a second end connected to the ring held on the foot strap;
  v) a plate in flat facing contact with and bonded to substantially all of the outside surface of the first portion of the foot strap,
    so that removing the weight of a person wearing the shoe and foot lift assist enables the elastic cord to lift the shoe and pivot the shoe upwardly to thereby enable the person to walk without the shoe toe end dragging on the ground and so that a person can walk on abrasive surfaces without causing wear to the foot strap.

3. The combination of claim 2 further comprising a heel band attached to the plate and looping around the shoe heel end to thereby aid in retaining the foot strap on the shoe.

4. A foot lift assist comprising:
a) a belt to be worn by a person and having opposed lateral sections;
b) a flexible foot strap having inside and outside surfaces and to be worn over the toes and forwardly of the ball of a foot of a person;
c) a ring held on the foot strap, the ring being at a location to the outside of a longitudinal centerline of a foot on which the foot strap is to be worn;
d) an elastic cord having a first end connected to a selected lateral section of the belt, and a second end connected to the ring on the foot strap, the elastic cord thereby extending between the belt and the foot strap ring solely on the outside of a leg and knee of a person wearing the foot strap and belt;
e) a pad on the foot strap inside surface and being located thereon to overlie a little toe of a person who wears the foot strap; and
f) a stress strip interposed between the flexible strap and the pad,
  so that removing the weight of a person from a foot that wears the foot strap enables the elastic cord to lift and bend the associated leg at the hip and knee and to pivot the foot upwardly to thereby enable the person to walk without the foot dragging on the ground and the stress strip reduces pressure on the little toe.

5. A foot lift assist comprising:
a) a belt to be worn by a person and having opposed lateral sections;
b) a flexible foot strap having inside and outside surfaces and to be worn over the toes and forwardly of the ball of a foot of a person;
c) a ring held on the foot strap, the ring being at a location to the outside of a longitudinal centerline of a foot on which the foot strap is worn;
d) an elastic cord having a first end connected to a selected lateral section of the belt, and a second end connected to the ring on the foot strap, the elastic cord thereby extending between the belt and the foot strap ring only on the outside of a leg and knee of a person wearing the foot strap and belt;
e) a plate bonded to the foot strap outside surface and underlying a foot of a person wearing the foot strap, wherein:
  i) the plate has a base and opposed sides upstanding from the base, each side having a slot therethrough; and
  ii) the strap passes through the slots in the plate sides; and
f) means for bonding the strap to the plate, so that a person can walk on abrasive surfaces without causing wear to the strap.

6. The foot lift assist of claim 5 further comprising a pair of inserts each secured to the foot strap between the foot strap and a respective one of the slots in the plate sides, the inserts preventing chafing of the foot strap on the plate sides at the slots.

7. Apparatus for assisting a person having a foot with foot drop to walk on a surface without dragging the toes on the surface comprising:
a) an elastic cord having a first end anchored to a belt to be worn by a person, and a second end;
b) a shoe having a sole with an upper surface and a walking surface, a heel end, and a toe end, the shoe having a widest portion between the heel and toe ends, and a toe region between the toe end and the shoe widest portion, the shoe defining a longitudinal centerline between the toe and heel ends that divides the shoe into an outside portion and an inside portion;

c) a foot strap worn around the shoe toe region and having an inside surface that is in contact with the shoe sole and an outside surface, a pad on the foot strap inside surface and having an end in flat facing contact with the sole upper surface to prevent the foot strap from slipping circumferentially around the shoe and d) means for connecting the elastic cord second end to the foot strap at a location on the outside portion of the shoe to thereby locate the elastic cord on the outside of a leg and knee of a person wearing the shoe, belt, elastic cord, and foot strap.

8. The apparatus of claim 7 further comprising a plate having first and second surfaces, the plate first surface being bonded to the strap outside surface such that the strap is between the shoe sole and the plate, so that the plate enables the person to walk on abrasive surfaces without causing wear to the strap.

9. The apparatus of claim 8 further comprising a heel band attached to the plate and looped around the shoe heel end.

10. Apparatus for assisting a person having a foot the surface comprising:

a) an elastic cord having a first end to be anchored at a hip associated with a foot having foot drop, and a second end;

b) a foot strap to be worn generally over the toes and forwardly of the ball of a foot, wherein the foot strap comprises:
i) a flexible strap having inside and outside surfaces and wrappable around a foot generally over the toes and forwardly of the ball of the foot, the flexible strap having a first portion that underlies a foot and a second portion that overlies a foot; and
ii) a pad on the flexible strap inside surface and located thereon to overlie a little toe of a foot wearing the foot strap;

c) a stress strip interposed between the flexible strap and the pad to distribute a force exerted on a little toe by the flexible strap when a person walks; and d) means for connecting the elastic cord second end to the foot strap at a location to the outside of a longitudinal centerline through a foot on which the foot strap is worn to thereby locate the elastic cord on the outside of a leg and knee of a person wearing the apparatus.

11. Apparatus for assisting a person having a foot with foot drop to walk on a surface without dragging the toes on the surface comprising:

a) an elastic cord having a first end to be anchored at a hip of a person, and a second end;

b) a foot strap to be worn generally over the toes and forwardly of the ball of a foot of a person, wherein the foot strap comprises:
i) a plate having first and second surfaces, wherein the plate has a base that underlies a foot of a person wearing the foot strap and opposite sides upstanding from the base, each side having a slot therethrough; and
ii) a strap bonded to the plate first surface and closeable on a foot of a person with the plate underlying the foot, the strap passing through the slots in the plate sides; and c) means for connecting the elastic cord second end to the foot strap at a location to the outside of a longitudinal centerline through a foot when the strap is worn to thereby locate the elastic cord on the outside of a leg and knee of a person wearing the apparatus.

12. The apparatus of claim 11 further comprising an insert operatively associated with each plate slot, each insert being secured to the strap to separate the strap from the associated plate slot and thereby protect the strap against chafing on the plate at the slots.

13. A method of assisting a person having a foot with foot drop to walk on a surface comprising the steps of:

a) wearing a shoe with a sole having a walking surface and an upper surface on a foot with foot drop;

b) wrapping a strap having inside and outside surfaces and a pad with first and second ends on the strap inside surface around the shoe;

c) contacting the upper surface of the sole of the shoe with the pad first end and locating the pad over a little toe of the foot when wrapping the strap around the shoe;

d) anchoring a first end of an elastic cord at a hip that is associated with the foot with foot drop;

e) connecting a second end of the elastic cord to the foot strap at a location that is to the outside of a longitudinal centerline of the foot wearing the foot strap and thereby locating the elastic cord on the outside of a leg and knee of a person with an uninterrupted span between the hip and foot;

f) removing the weight of the person from the foot; and g) exerting an upward force on the foot and bending the leg at the knee and hip and simultaneously pivoting the foot and the ankle and thereby enabling the person to take a step without the toes dragging on the surface.

14. A method of assisting a person having a foot with foot drop to walk on a surface comprising the steps of:

a) anchoring a first end of an elastic cord at a hip that is associated with the foot of a person with foot drop;

b) wrapping a strap having inside and outside surfaces and an abrasion resistant material on the outside surface and a pad on the inside surface and a stress strip between the strap and the pad and over the toes and forwardly of the ball of the foot with foot drop, and locating the pad over the little toe of the foot and locating the abrasion resistant material under the foot;

c) connecting a second end of the elastic cord to the foot strap at a location that is to the outside of a longitudinal centerline of the foot and thereby locating the elastic cord on the outside of the leg and knee of the person between the hip and foot;

d) removing the weight of the person from the foot;

e) exerting an upward force on the foot and bending the leg at the knee and hip and simultaneously pivoting the foot at the ankle and thereby enabling the person to take a step without the toes dragging on the surface;

f) contacting the surface with the abrasion resistant material when the person walks and thereby reducing ear and slipping of the fully flexible strap on the surface; and g) distributing the force exerted on the little toe of the foot by means of the stress strip when the person walks.

* * * * *